US006547804B2

United States Patent
Porter et al.

(10) Patent No.: US 6,547,804 B2
(45) Date of Patent: Apr. 15, 2003

(54) SELECTIVELY PERMEABLE HIGHLY DISTENSIBLE OCCLUSION BALLOON

(75) Inventors: Stephen Christopher Porter, Fremont, CA (US); Thomas Yung-Hui Chien, San Jose, CA (US); Huey Quoc Chan, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 73 days.

(21) Appl. No.: 09/748,972

(22) Filed: Dec. 27, 2000

(65) Prior Publication Data

US 2002/0082638 A1 Jun. 27, 2002

(51) Int. Cl.[7] ............................................. A61M 29/02
(52) U.S. Cl. ...................................................... 606/195
(58) Field of Search .............................. 606/191, 192, 606/194, 195, 198, 200

(56) References Cited

U.S. PATENT DOCUMENTS

| | | | |
|---|---|---|---|
| 4,327,734 A | | 5/1982 | White, Jr. .................... 128/325 |
| 4,364,392 A | * | 12/1982 | Strother et al. ......... 604/103.01 |
| 4,402,319 A | | 9/1983 | Handa et al. |
| 4,819,637 A | * | 4/1989 | Dormandy et al. .......... 137/846 |
| 5,122,136 A | | 6/1992 | Guglielmi et al. |
| 5,181,921 A | * | 1/1993 | Makita et al. ............... 604/247 |
| 5,350,397 A | | 9/1994 | Palermo et al. |
| 5,639,277 A | * | 6/1997 | Mariant et al. .............. 606/191 |
| 5,779,672 A | * | 7/1998 | Dormandy, Jr. ........... 604/99.04 |
| 6,077,260 A | | 1/2000 | Wheelock et al. |
| 6,083,220 A | | 7/2000 | Guglielmi et al. |
| 6,123,714 A | | 9/2000 | Gia et al. |
| 6,165,193 A | | 12/2000 | Green, Jr. et al. |
| 6,299,627 B1 | * | 10/2001 | Eder et al. ................... 606/191 |

FOREIGN PATENT DOCUMENTS

| | | |
|---|---|---|
| WO | 98/57586 | 12/1998 |
| WO | 00/27292 | 5/2000 |

\* cited by examiner

*Primary Examiner*—John J. Calvert
*Assistant Examiner*—Shaun R Hurley
(74) *Attorney, Agent, or Firm*—Vidas, Arrett & Steinkraus

(57) ABSTRACT

A process and apparatus for occluding a vascular site. A catheter having a highly distensible occlusion balloon detachably mounted at a distal end thereof is provided to the vascular site and at least partially filled with an aqueous balloon inflation fluid which allows the balloon placement to be imaged. The balloon is porous to the aqueous inflation fluid and the inflation fluid is gradually displaced through the balloon pores by a liquid filling composition which is solidifiable on contact with the aqueous inflation fluid to produce a mass to which the balloon is nonporous. The filing composition is injected to bring the balloon wall into contact with the vessel wall at the vascular site. The balloon is detached from the catheter after the filling composition has at least substantially solidified and the catheter removed from the body.

46 Claims, 4 Drawing Sheets

SELECTIVELY PERMEABLE HIGHLY DISTENSIBLE OCCLUSION BALLOON

A known treatment for aneurysms, particularly intercranial berry aneurysms, utilizes a balloon to fill and occlude the aneurysm. In such procedures the interior of the aneurysm is entered through the use of a microcatheter, typically fed along a guide wire which allows navigation into the cerebral arteries and entry into a cranial aneurysm. A balloon is attached to the end of the microcatheter and introduced into the aneurysm. The balloon is inflated and detached within the aneurysm, where it is left to occlude the sac and neck while preserving blood flow in the parent artery.

U.S. Pat. No. 4,364,392 describes an occlusion balloon which is delivered via a catheter to the occlusion site. Upon delivery, the balloon is inflated with a suspension of small solid particles in a carrier liquid. The balloon is made porous so that the carrier liquid perfuses through the balloon wall, shrinking the balloon over the solid, incompressible particles. A ridge/groove fitting releases the balloon from the catheter upon application of a sufficient pulling force.

U.S. Pat. No. 4,402,319 describes a balloon catheter having a portion at the joint between the catheter and the balloon which is cuttable by torsion or by heating to allow the balloon to be released from the catheter and remain behind to embolize a vascular lesion. The balloon may be initially inflated using a first fluid containing a contrast media so that the balloon location may be confirmed and adjusted as needed, after which it is deflated to remove the first fluid. A catalyzed curable liquid is then injected into the balloon where it polymerizes to form a solid before the balloon body is detached from the catheter.

U.S. Pat. No. 4,819,637 describes a releasable occlusion balloon which includes a friction-fit catheter mounting and a one-way valve allowing the balloon to be filled with a non-solidifying liquid.

U.S. Pat. No. 5,191,921 and U.S. Pat. No. 5,779,672 describe releasable occlusion balloons which use a pair of self sealing one-way valves to allow passage of a guide wire through the balloon and to allow the balloon to be filled with a non-solidifying liquid.

Thrombogenic coil devices which may be delivered via a catheter to an occlusion site and left there are also known. Examples of such devices are described in U.S. Pat. No. 5,122,136, U.S. Pat. No. 5,350,397, U.S. Pat. No. 6,077,260, U.S. Pat. No. 6,083,220 and U.S. Pat. No. 6,123,714. Detachment mechanisms include electrolytic corrosion of a metal member and a ball joint released by a pusher mechanism.

All patents, other publications or copending applications mentioned anywhere in this application are expressly incorporated herein by reference in their entirety.

SUMMARY OF THE INVENTION

The present invention pertains to an occlusion balloon, a filling method therefor, and an occlusion mass formed therefrom.

In one aspect the invention comprises a releasable occlusion balloon made of a material which is porous to aqueous media and/or non-viscous liquid and which is substantially non-porous to hydrophobic and/or viscous material. The balloon wall material is preferably highly distensible so that it can readily conform to the aneurysm at very low pressure inflation and without distention of the aneurysm. The balloon wall may be a hydrogel material. The balloon wall may be biodegradable or coated with a biodegradable material.

The balloon is initially located in the aneurysm and at least partially inflated with an aqueous inflation fluid. The aqueous inflation fluid suitably includes a contrast agent which allows the location of the balloon to be confirmed and adjusted as needed. Once the location is determined to be satisfactory, the aqueous inflation fluid is gradually displaced, without deflating the balloon, with a second liquid comprising a solidifying non-aqueous or viscous material. The aqueous material passes through the balloon wall and into the bloodstream. In this way the initial location of the balloon is maintained. When the aqueous inflation fluid has been fully displaced, the balloon may be further inflated with the second liquid, if necessary to fill the aneurysm. Upon solidification of the solidifying material, the balloon may be detached in conventional manner and the catheter withdrawn, leaving the balloon in place.

The solidifying material is preferably one in which solidification is initiated by contact with water or saline.

DESCRIPTION OF THE PREFERRED EMBODIMENTS

Figure 1A:
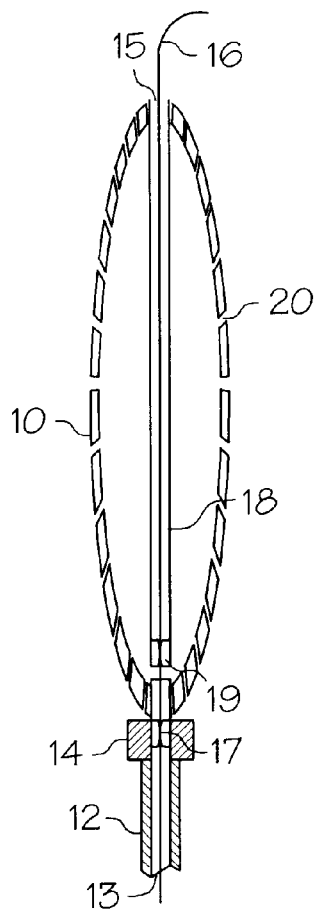
FIG. 1a is a fragmentary schematic cross-sectional view of a catheter/balloon assembly of the invention threaded over a guide wire.

The balloon of the invention preferably is both porous and highly distensible. The porous material allows aqueous inflation fluid to pass though the balloon wall at low pressure. The porosity may be in the form of pin-holes, microscopic physical channels or molecular channels (e.g. through a hydrogel wall). Desirably the porosity is such that a of volume of a 50/50 saline/contrast mixture which is equal to that of the nominally filled balloon will pass through the wall in a period not exceeding 30 minutes, preferably 5 minutes. Suitably the holes or channels have a size which is about 20 $\mu$m or less.

By "highly distensible" in this case, is meant that the material can be filled to its nominal or molded dimension and then further distended to contact the vessel wall at only slightly above nominal pressure, i.e. not more 70.0 kPa (525.0 mm Hg) above vascular pressure, more preferably from about 1 kPa (7.5 mm Hg) to about 25 kPa (188 mm Hg) above vascular pressure. Preferably the distention is in the range of 150 to 400% at 70.0 kPa. The balloon material should be flexible enough to allow the balloon to be inflated to its nominal dimension at a differential pressure of less than one kPa (<7.5 mm Hg).

Suitable balloon wall materials include latex (natural rubber), polyisoprene, styrene-ethylene-butylene-styrene block copolymer (SEBS), other synthetic rubbers, polyurethanes, silicones and other flexible and elastic biocompatible polymers. The balloon wall material may be a hydrogel, or a polymer material which forms a hydrogel when it contacts an aqueous fluid. Balloon wall thickness is suitably in the range of 0.005 inches (0.127 mm) or thinner, more preferably from about 0.001 inches (25.4 µm) to about 0.00025 inches (6.4 µm).

Porosity can be introduced into the balloon wall in a number of ways. Laser cutting can be used to introduce pores in a non-porous balloon. Alternatively, a non-porous balloon may be masked using a mesh having openings of the desired pore size, and then bombarded with high energy ions in an ion implantation chamber to perforate the balloon wall under the openings in the mask.

In another alternative procedure for forming a porous balloon, dissolvable or etchable particles (Porogens) can be mixed with a liquid polymer emulsion from which the balloon is formed and the mixture poured into a balloon mold or dip-coated from a solvent mixture. After the material has cured, the particles or fibers embedded in the walls of the balloon can be dissolved with water or a suitable solvent or chemically etched out. Suitable porogens include salts, alcohol/water soluble polymers, other materials that can be dissolved with a solvent that does not affect the balloon material, atomized aluminum powder, glass micropheres, calcium carbonate particles, or nylon fibers. Balloons formed by blowing a polymer extrusion can be similarly manufactured by adding such dissolvable/etchable particles or fibers to the polymer melt before extrusion and dissolving or etching the porogen material after the balloon has been blown.

A suitable balloon can be prepared from polyisoprene by injection molding a balloon with a wall thickness of and 0.001 inches, adding pores by laser cutting holes of 10 µm diameter.

The material of the walls of the balloon can also be impregnated or coated with a radiopaque or magnetic responsive material to aid in guiding the catheter to the desired position using X-ray fluoroscopy or NMR imaging, respectively.

Figure 1B:
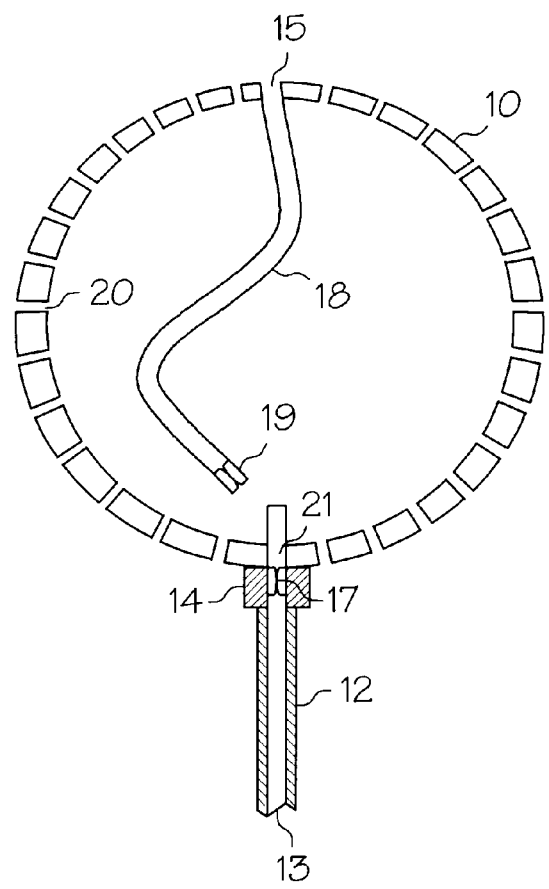
FIG. 1b is a fragmentary schematic cross-sectional view of a catheter/balloon assembly as in FIG. 1 in an inflated condition, with guide wire withdrawn.

A preferred embodiment of the inventive balloon is shown in FIGS. 1a and 1b. Balloon 10 is mounted on a catheter 12 via a detachment mechanism 14. The detachment mechanism may operate by mechanical, thermal, electrolytic or any other means to allow the balloon to be detached from the catheter and left in place at the site of occlusion. The catheter includes at least one lumen 13 through which a inflation fluid may be provided to the balloon and through which the catheter may be guided to the occlusion site via a guide wire 16. The guide wire 16 passes into the balloon through a self-sealing check valve 17 or other sealing device of known configuration. A tubular stiffening member 18, suitably having a thicker wall than the balloon outer wall, or made of a polymer material which is flexible, but more rigid than the balloon material, extends inwardly from the distal end 15 of the balloon 10, terminating in a valve or like sealing device 19. The guide wire 16 passes out of the balloon 10 via exit valve 19 and the inner lumen of stiffening member 18. The stiffening member 18 provides compressive stiffening support to allow delivery of the of the balloon to the aneurysm along the guide wire in a stretched/fully extended state. Upon retraction of the guide wire, the check valves 17, 19 operate to selectively close the balloon openings, allowing it to be filled by inflation fluid and, subsequently solidifying fluid. The balloon 10 includes a plurality of pores 20 through which an aqueous inflation fluid can be perfused. FIG. 1b shows the balloon of FIG. 1a, after retraction of the guide wire in an inflated configuration. The stiffening member 18 floats freely within the inflated balloon.

In an alternative embodiment, not shown, the stiffening member 18 may project inwardly into the balloon from the distal end 21 of the inflation lumen, instead of balloon distal end 15. A guide wire exit valve may be mounted in the balloon wall at end 15 and exit valve 19 may optionally be removed. In yet a further alternative embodiment member 18 is shortened and a second stiffening member is provided projecting inwardly from lumen end 21 is provided to contact the shortened member 18 when the guide wire is present to effect compressive stiffening. In other alternative embodiments exit valve 19 may be moved to the distal end of the balloon or an intermediate location on member 18.

FIGS. 2–6 illustrate various stages of a preferred process for filling and installation of a balloon 22 similar to balloon 10, except that the stiffening member is not present and a guide wire exit valve 23 is located on the distal end of the balloon to allow passage of the guide wire therethrough. Balloon 22 is shown in various stages after the balloon and catheter assembly has been delivered to an aneurysm 25 and the guide wire withdrawn.

Figure 2:
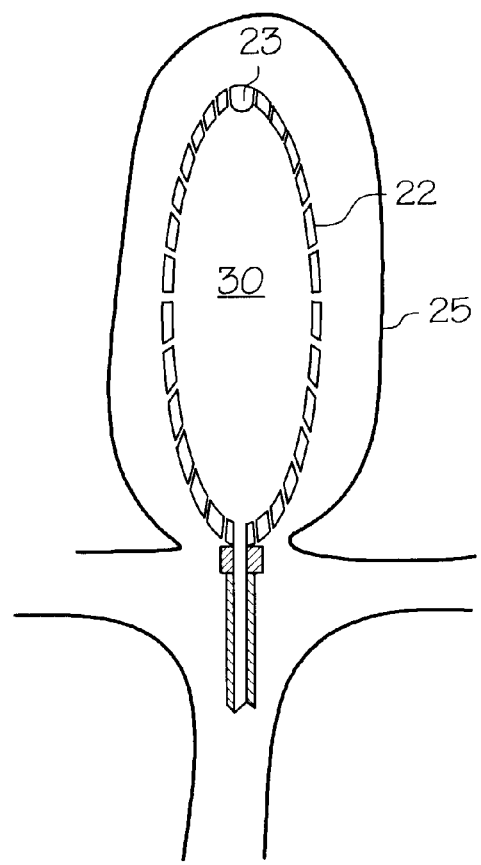
FIG. 2 is a fragmentary schematic cross-sectional view of a catheter/balloon assembly of the invention located in a vascular aneurysm and inflated to a nominal dimension with an aqueous inflation fluid.
Figure 3:
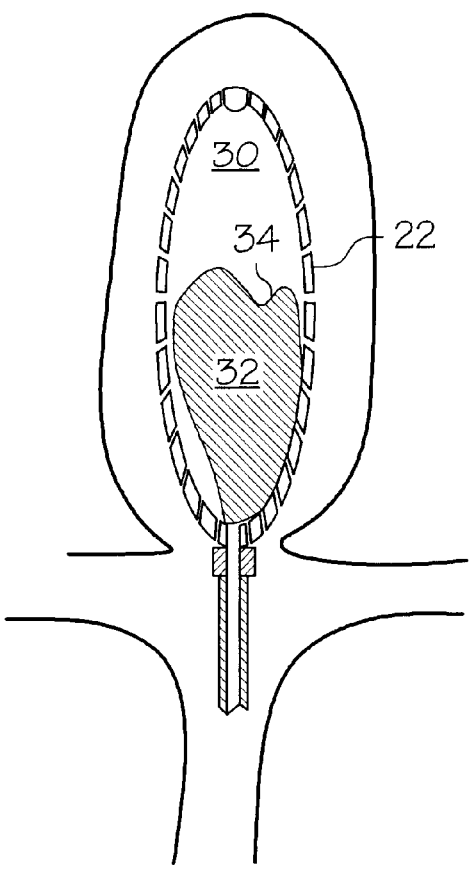
FIG. 3 is a view as in FIG. 2 with the inflation fluid partially displaced with a solidifiable filling fluid.

The filling and installation process begins as shown in FIG. 2 by filling the balloon with an aqueous inflation fluid 30. The fluid suitably may be saline or blood plasma and/or desirably includes a contrast agent which allows radiographic or magnetic imaging. The contrast agent allows the location of the balloon to be confirmed before the solidifying material is injected.

Once the location has been confirmed, a solidifying fluid 32 is injected displacing the initial inflation fluid 30 which perfuses through the balloon walls without replenishment. The solidifying fluid 32 preferably is one for which solidification is initiated by contact with the aqueous inflation fluid 30 and forms an expanding polymeric skin 34 as the fluid 32 is injected. Additionally the solidifying fluid is desirably provided with a different degree of radiographic or magnetic contrast. The skin 34 functions to maintain a phase separation so that the aqueous inflation fluid 30 will be substantially completely forced out of the balloon and, together with the differing contrast between the fluids 30 and 32, allows the filling process to monitored by the imaging apparatus.

Fluid 32 may be a polymerizable liquid which is initiated by contact with an aqueous solution, or a polymer solution which precipitates the polymer upon contact with an aqueous solution. Preferably the polymer or polymer formulation produced or precipitated is soft and flexible and allows continued expansion of the polymer mass as the fluid 32 is injected. An example of a polymerizable liquid is a cyanoacrylate formulation such as TRUFILL, an n-butyl cyanoacrylate formulation sold by Cordis, or NEURACRYL, a developmental product from Provasis Med. Corp., El Caton Calif., or other cyanoacrylate based matter. Polymer solutions may be solutions of a polymer in a biocompatible water soluble solvent, for instance an ethylene-vinyl alcohol polymer dissolved in water soluble solvent dimethyl sulfoxide such as sold under the trademark ONYX, by Micro Therapeutics Inc., Irving Calif.

Figure 4:
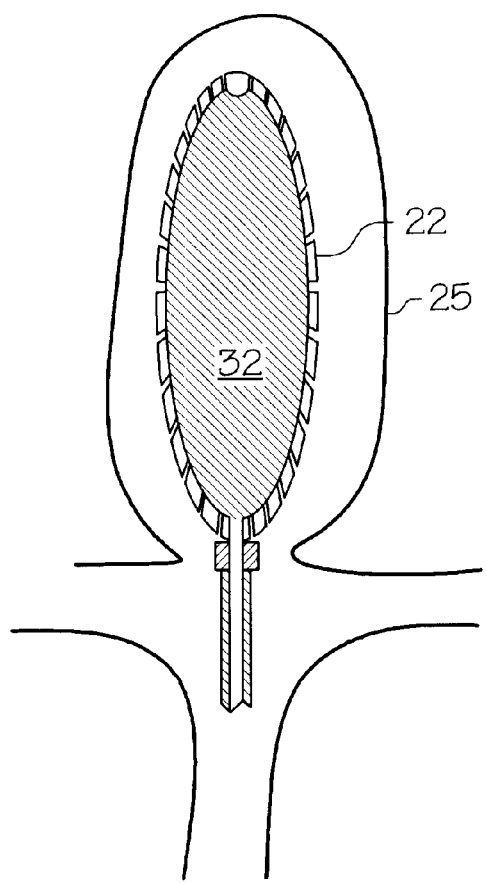
FIG. 4 is a view as in FIG. 3 with the inflation fluid completely displaced.

As shown in FIG. 4, when fluid 32 has fully displaced the aqueous inflation fluid 30, at least the polymer component (or polymerization product) is confined within the balloon. (In the case that fluid 32 comprises a water soluble solvent, such solvent may continue to be lost). The polymer confinement may be because of a balloon wall hydrophobicity, high viscosity of the fluid 32, or polymer produced therefrom, or simply the pluging of the pores 20 as the polymer contacts the balloon wall. In most cases more than one such mechanism will be effective to confine the polymer mass within the balloon wall.

Figure 5:
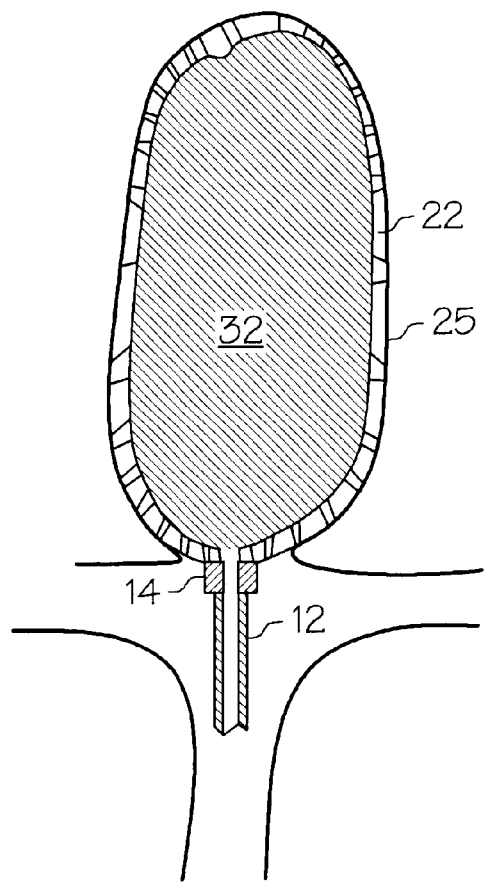
FIG. 5 is a view as in FIG. 4 with the balloon further distended to contact the walls of the aneurysm.
Figure 6:
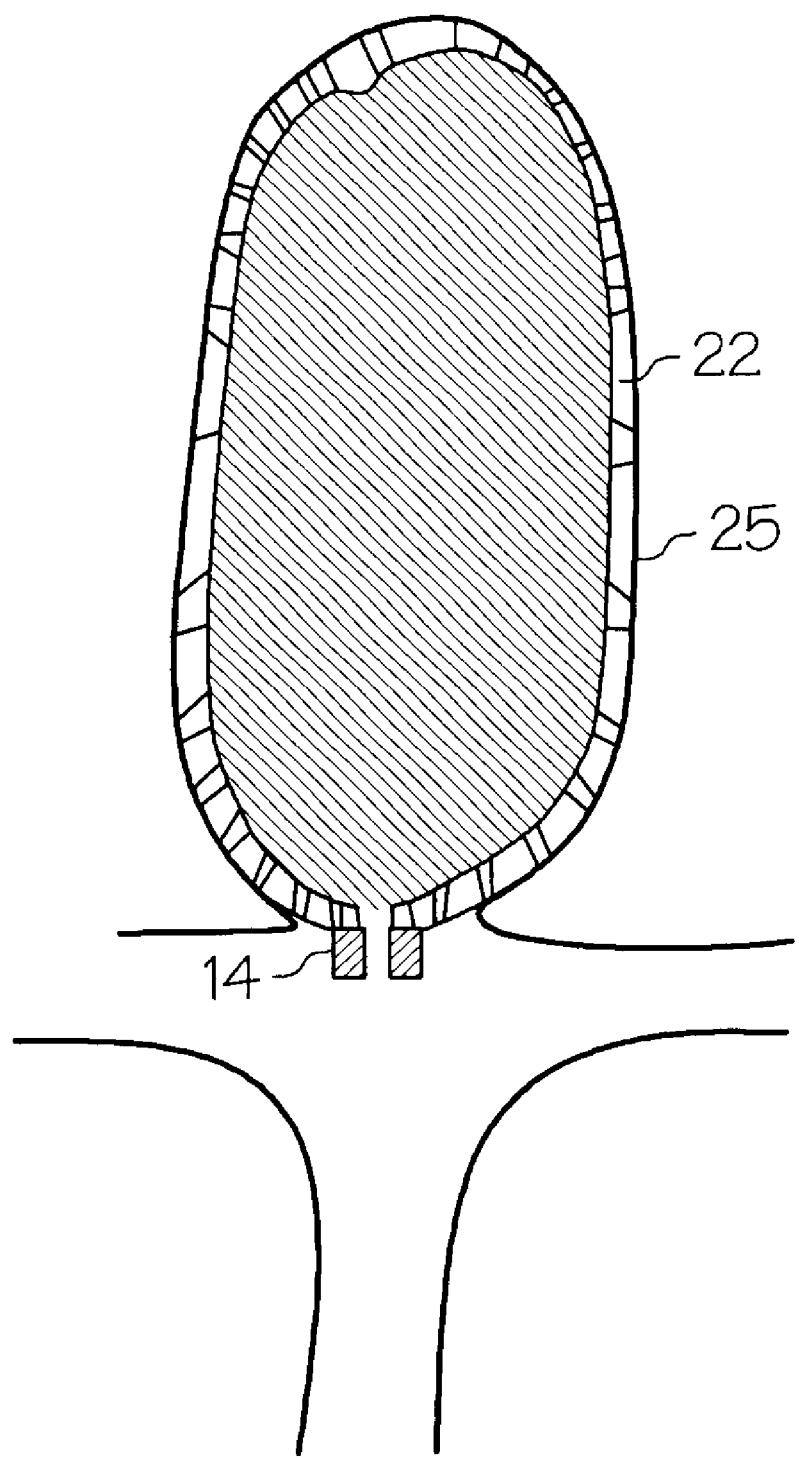
FIG. 6 is a view as in FIG. 5, but with the catheter having been separated and removed after solidification of the filling fluid.

Referring to FIG. 5, as further fluid 32 is injected into balloon 22, the balloon wall is expanded under very low additional pressure as described above, until the aneurysm has been substantially filled by the balloon. Preferably the balloon wall material is sufficiently distensible, and the pressure of expansion is sufficiently low, that the aneurysm wall will not be distorted when the balloon contacts the aneurysm wall and instead, the balloon conforms itself to the aneurysm morphology.

In the final step the balloon is separated from the catheter by activating the detachment mechanism 14 and the catheter is withdrawn. The polymer filled balloon is left behind, occluding the aneurysm.

The detachment mechanism may be constructed in any known way which allows separation of a occlusion balloon or other occlusion device from a catheter. In particular, in addition to mechanisms known for occlusion balloons, detachment mechanisms used with trombogenic coil devices as described above may be readily adapted for use with the balloons of the invention without undue experimentation. Separation may be provided by mechanical action such as twisting or pulling, by thermal action such as by melting a low melting linkage or by chemical action, such as by electrolytic corrosion of a thin metal linkage.

An alternative method of deployment does not require full inflation of the balloon to its molded morphology and then beyond. Due to the generally non-spherical and sometimes elongated nature of aneurysms in some cases it may be preferred to have the device fully expanded in certain areas and under-inflated in others. Suitably the nominal size (inflated but at zero differential pressure) would be equal to the largest dimension of the aneurysm. For example if the aneurysm is 6 mm×9 mm (W×H) then a 9 mm balloon would be used. This also reduces the fully inflated pressure required for filling of the aneurysm.

Bioactive compounds may be impregnated in either the balloon or incorporated into the formulation of the solidifying material 32 to allow controlled release of the medication into the bloodstream. If immediate medication is indicated at the aneurysm site at the time of introducing the balloon, such medication may be introduced in the aqueous inflation fluid 30 which is initially introduced into the balloon and perfused through the balloon wall into the bloodstream along with fluid 30. A bioactive substance may also be entrained in the balloon wall.

The bioactive substance may be one which encourages tissue ingrowth into the aneurysm. Such tissue stimulating substances substance may be incorporated either within the balloon material or within the embolic. The balloon device may only need to be inflated to the point where it has occluded the aneurysmal neck and has contacted the aneurysmal wall at a number of points and with sufficient force as to allow the device to become firmly placed. The unfilled areas within the aneurysm may be filled in with time by ingrowth of stimulated tissues.

In another variation of the invention, the balloon inflation fluid 30 may incorporate a chemical or radio-emissive substance that would initiate or serve as a catalyst for or is a reactant in the process required for the solidification of the liquid embolic material. Some or all of the balloon inner surface may be coated with, or have incorporated therein, such a catalytic or initiating substance. Also, any of the other structural elements of the device may have such a catalytic or initiating substance incorporated therein or coated thereon.

While the balloon and process of the invention has been illustrated with respect to the treatment of an aneurysm, it should be understood that other balloon configurations may be employed and other defects may be treated using the inventive balloon and process. For instance, a balloon as already described may be used to occlude the main channel of a vessel in a situation where it is desired to close the vessel. Such a situation may be indicated to deprive a cancer of blood flow. In another alternative treatment situation, a weakened vessel wall can be treated with a balloon in a toroid shape. Such a balloon is inflated to only partially occlude the vessel, allowing blood to flow through the center opening of the toroid.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 5 may be taken as alternatively dependent on claim 2, claim 3 or claim 4; claim 12 may be taken as alternatively dependent from claim 11; etc.).

What is claimed is:

1. A vascular occlusion balloon, the balloon having a proximal and a distal end, a guide wire entry port providing passage into the balloon at the proximal end, a guide wire exit port providing passage out of the balloon at the distal end, the balloon characterized in that it further comprises a flexible tubular stiffening member extending inwardly from at least one of the proximal or a distal end thereof and defining a guide wire lumen within at least a portion of the interior of the balloon.

2. A balloon as in claim 1 wherein a check valve is located at said distal end of the balloon or within a portion of said stiffening member extending inwardly from said distal end of the balloon, the valve operable to permit a guide wire to pass therethrough and to seal the balloon distal end when the guide wire is not present.

3. A balloon as in claim 2 further comprising a second check valve located at said proximal end or within a portion of said stiffening member extending inwardly from said proximal end of the balloon, the valve operable to permit a guide wire to pass therethrough and to permit injection of fluids into the balloon but to seal the balloon against fluid egress from the balloon therethrough.

4. A balloon as in claim 1 wherein the balloon wall is porous to an aqueous inflation fluid.

5. An occlusion balloon as in claim 4 wherein the balloon wall has a porosity which permits transport of said inflation fluid therethrough at a rate of at least 10 µl/min per cm$^2$ at a differential pressure of 5 kPa.

6. An occlusion balloon as in claim 4 wherein the balloon wall has a porosity which permits transport of one nominal volume of said inflation fluid therethrough within a period not exceeding 30 minutes at said differential pressure.

7. An occlusion balloon as in claim 1 the balloon being further characterized in that it inflates to a dimension at least 150% beyond nominal diameter at a differential pressure of not more than 70.0 kPa above vascular pressure.

8. A balloon as in claim 1 having incorporated therein or thereon a bioactive material to encourage tissue ingrowth.

9. A balloon as in claim 1 having a material which catalyzes or initiates solidification of a solidifiable material when the balloon is filled therewith coated on an interior surface thereof, or incorporated into a substructure thereof.

10. A balloon as in claim 1 filled with a solidified mass of polymer material.

11. A balloon as in claim 10 wherein said polymer material includes a radiographic or magnetic contrast agent.

12. A catheter assembly comprising a balloon as in claim 1 mounted on the end of a catheter.

13. A catheter assembly as in claim 12 the assembly further comprising a detachment mechanism for releasing the balloon from the catheter at a selected deployment site within the body.

14. A vascular occlusion balloon adapted for deployment in the body in a condition in which the balloon is at least partially filled with solid material, the balloon characterized by having an activator material coated on an interior surface thereof, or incorporated into a substructure thereof, the activator material being one which catalyzes or initiates solidification of a solidifiable material with which the balloon can be at least partially filled when deployed.

15. A vascular occlusion balloon as in claim 14 wherein the balloon wall is porous to an aqueous inflation fluid.

16. An occlusion balloon as in claim 15 wherein the balloon wall has a porosity which permits transport of said inflation fluid therethrough at a rate of at least 10 µl/min per cm$^2$ at a differential pressure of 5 kPa.

17. An occlusion balloon as in claim 15 wherein the balloon wall has a porosity which permits transport of one nominal volume of said inflation fluid therethrough within a period not exceeding 30 minutes at said differential pressure.

18. An occlusion balloon as in claim 14 the balloon being further characterized in that it inflates to a dimension at least 150% beyond nominal diameter at a differential pressure of not more than 70.0 kPa above vascular pressure.

19. An occlusion balloon as in claim 18 wherein said differential pressure is from 1 to about 3 kPa above vascular pressure.

20. An occlusion balloon as in claim 19 expandable beyond its nominal diameter to a dimension of from 150 to 400% at said differential pressure.

21. A balloon as in claim 14 having incorporated therein or thereon a bioactive material to encourage tissue ingrowth.

22. A catheter assembly comprising a balloon as in claim 14 mounted on the end of a catheter.

23. A catheter assembly as in claim 22 further comprising a detachment mechanism for releasing the balloon from the catheter at a selected deployment site within the body.

24. A catheter assembly as in claim 22 adapted for sliding over a guide wire, the balloon having a proximal end and a distal end, the guide wire passing into the balloon at the proximal end and out of the balloon at the distal end when in use, the balloon characterized in that it further comprises a flexible tubular stiffening member extending inwardly from at least one of the proximal or a distal end thereof and defining a guide wire lumen within at least a portion of the interior of the balloon.

25. An occlusion balloon as in claim 10 wherein the balloon wall is formed of a material selected from the group consisting of latex, polyisoprene, SEBS, synthetic rubbers, polyurethanes, silicones, and hydrogels.

26. An occlusion balloon as in claim 10 wherein said inflation fluid is selected from the group consisting of saline solution, blood plasma and mixtures thereof with a radiographic or magnetic contrast media.

27. An occlusion balloon as in claim 10 wherein the balloon has a wall which is flexible enough to permit the balloon to be inflated to its nominal dimension at a differential pressure of not more than 1 kPa.

28. An implanted balloon filled with a solidified mass of polymer material, obtained by filling a balloon has in claim 14 with said solidifiable material.

29. An implanted balloon as in claim 28 wherein said polymer material includes a radiographic or magnetic contrast agent.

30. An implanted balloon as in claim 28 located within an vascular aneurysm, the balloon and solidified mass conforming to the configuration of the aneurysm.

31. A vascular occlusion balloon having coated on a surface thereof, or incorporated into a substructure thereof, a bioactive material to encourage tissue ingrowth; further having a material which catalyzes or initiates solidification of a solidifiable material when the balloon is filled therewith, coated on an interior surface thereof, or incorporated into a substructure thereof.

32. A balloon as in claim 31 at least partially filled with a solidified mass of polymer material.

33. A balloon as in claim 32 wherein said polymer material includes a radiographic or magnetic contrast agent.

34. A balloon as in claim 32 located within an vascular aneurysm, the balloon and solidified mass conforming to the configuration of the aneurysm.

35. A catheter assembly comprising a balloon as in claim 31 mounted on the end of a catheter.

36. A catheter assembly as in claim 35 further comprising a detachment mechanism for releasing the balloon from the catheter at a selected deployment site within the body.

37. A process for occluding a vascular site comprising
 a) providing
  a catheter having a highly distensible occlusion balloon detachably mounted at a distal end thereof;
  an aqueous balloon inflation fluid, the balloon being porous to the aqueous inflation fluid; and
  a liquid filling composition which is solidifiable on contact with the aqueous inflation fluid to produce a mass to which the balloon is nonporous;
 b) advancing the catheter through the vascular system to locate the balloon at the vascular site;

c) at least partially inflating the balloon with the inflation fluid and confirming the balloon location;

d) injecting the filling composition, to displace the inflation fluid through the balloon pores until the balloon has been emptied of inflation fluid and to bring the balloon wall into contact with the vessel wall at said vascular site;

e) detaching the balloon from the catheter after the filling composition has at least substantially solidified; and f) removing the catheter from the body.

38. A process as in claim 37 wherein the balloon is characterized in that it inflates to a dimension at least 150% beyond nominal diameter at a differential pressure of not more than 70.0 kPa above vascular pressure.

39. A process as in claim 37 wherein the balloon wall has a porosity which permits transport of said inflation fluid therethrough at a rate of at least 10 $\mu$l/min per cm$^2$ at a differential pressure of 5 kPa.

40. A process as in claim 37 wherein the balloon wall has a porosity which permits transport of one nominal volume of said inflation fluid therethrough within a period not exceeding 30 minutes at said differential pressure.

41. A process as in claim 37 wherein said inflation fluid is selected from the group consisting of saline solution, blood plasma and mixtures thereof with a radiographic or magnetic contrast media.

42. A process as in claim 37 wherein the balloon wall is flexible enough to permit the balloon to be inflated to its nominal dimension at a differential pressure of not more than 1 kPa.

43. A process as in claim 37 wherein the balloon has incorporated therein or thereon a bioactive material to encourage tissue ingrowth.

44. A process as in claim 37 wherein the balloon has a material which catalyzes or initiates solidification of a solidifiable material when the balloon is filled therewith coated on an interior surface thereof, or incorporated into a substructure thereof.

45. A process as in claim 37 wherein the liquid filling composition includes a radiographic or magnetic contrast agent.

46. A process as in claim 37 wherein the catheter is adapted for sliding over a guide wire, the balloon having a proximal and a distal end, the guide wire passing into the balloon at the proximal end and out of the balloon at the distal end when in use, the balloon being further characterized in that it further comprises a flexible tubular stiffening member extending inwardly from at least one of the proximal or a distal end thereof and defining a guide wire lumen within at least a portion of the interior of the balloon.

* * * * *